(12) United States Patent
Boumsellek et al.

(10) Patent No.: US 9,310,335 B2
(45) Date of Patent: Apr. 12, 2016

(54) DUAL POLARITY SPARK ION SOURCE

(71) Applicant: Implant Sciences Corporation, Wilmington, MA (US)

(72) Inventors: Said Boumsellek, San Diego, CA (US); Dmitriy V. Ivashin, Peabody, MA (US)

(73) Assignee: Implant Sciences Corporation, Wilmington, MA (US)

( * ) Notice: Subject to any disclaimer, the term of this patent is extended or adjusted under 35 U.S.C. 154(b) by 0 days.

(21) Appl. No.: 14/317,133

(22) Filed: Jun. 27, 2014

(65) Prior Publication Data

US 2015/0001387 A1     Jan. 1, 2015

Related U.S. Application Data

(60) Provisional application No. 61/840,050, filed on Jun. 27, 2013.

(51) Int. Cl.
*G01N 27/62* (2006.01)

(52) U.S. Cl.
CPC ................... *G01N 27/622* (2013.01)

(58) Field of Classification Search
USPC ............. 250/282, 286, 288, 423 R, 287, 281, 250/290, 291
See application file for complete search history.

(56) References Cited

U.S. PATENT DOCUMENTS

| | | | |
|---|---|---|---|
| 5,969,349 A | 10/1999 | Budovich et al. | |
| 6,429,426 B1 | 8/2002 | Döring | |
| 6,969,851 B1 * | 11/2005 | Sheen | G01N 23/00 250/286 |
| 7,105,808 B2 | 9/2006 | Bromberg et al. | |
| 8,173,959 B1 | 5/2012 | Boumsellek et al. | |
| 8,440,981 B2 | 5/2013 | Bromberg et al. | |
| 8,608,826 B2 * | 12/2013 | Al-Hamouz | 95/2 |
| 2007/0007448 A1 | 1/2007 | Wang | |
| 2007/0023630 A1 | 2/2007 | Malek et al. | |
| 2007/0040111 A1 | 2/2007 | Jill et al. | |
| 2009/0238723 A1 * | 9/2009 | Guharay | G01N 21/658 422/68.1 |
| 2010/0032580 A1 * | 2/2010 | Caporaso | H01J 27/26 250/396 R |
| 2012/0056085 A1 | 3/2012 | Giles et al. | |
| 2012/0273669 A1 | 11/2012 | Ivashin et al. | |
| 2012/0326020 A1 | 12/2012 | Ivashin et al. | |

OTHER PUBLICATIONS

U.S. Appl. No. 13/858,417, filed Apr. 8, 2013, Ivashin et al.

* cited by examiner

*Primary Examiner* — Phillip A Johnston
*Assistant Examiner* — Hsien Tsai
(74) *Attorney, Agent, or Firm* — Muirhead and Saturnelli, LLC

(57) ABSTRACT

Devices and techniques for ion analysis, including ion mobility separation and mass spectrometry, are provided using a dual polarity spark ion source and having the flexibility required to optimize the detection performance for a broad range of illicit substances with different physical and chemical properties. In various embodiments, the volatility and electro-chemical aspects may be addressed by the system described herein by performing real-time detection of compounds detectable in both positive and negative polarities and/or prioritizing spectra acquisition in a given polarity due to the high volatility and therefore short residence of certain target compounds.

29 Claims, 6 Drawing Sheets

DUAL POLARITY SPARK ION SOURCE

RELATED APPLICATIONS

This application claims priority to U.S. Provisional App. No. 61/840,050, filed Jun. 27, 2013, entitled "Dual Polarity Ion Mobility Spectrometer Using Spark Ionization," which is incorporated herein by reference.

TECHNICAL FIELD

This application is related to the field of chemical analysis and, in particular, ion mobility spectrometry.

BACKGROUND OF THE INVENTION

In field applications, chemical analysis instruments may be confronted with various complex mixtures regardless of indoor or outdoor environments. Such mixtures may cause instrument contamination and confusion due to the presence of molecular interferents producing signatures that are either identical to that of the chemical compounds of interest or unresolved by the analytical instrument due to its limited resolution. An interferent can also manifest its presence by affecting the limit of detection of the compound of interest. A multi-stage analysis approach may be used to reduce the chemical noise and produce enough separation for deterministic detection and identification. The multi-stage analysis may include either a single separation technique such as mass spectrometry (MS) in MS$^n$ instruments or a combination of different separation techniques.

Ion mobility spectrometry (IMS) utilizes relative low electric fields to propel ions through a drift gas chamber and separate these ions according to their drift velocity. In IMS, the ion drift velocity is proportional to the field strength and thus an ion's mobility (K) is independent of the applied field. In the IMS both analyte and background molecules are typically ionized using radioactive alpha or beta emitters and the ions are injected into a drift tube with a constant low electric field (300 V/cm or less) where they are separated on the basis of their drift velocity and hence their mobility. The mobility is governed by the ion collisions with the drift gas molecules flowing in the opposite direction. The ion-molecule collision cross section depends on the size, the shape, the charge, and the mass of the ion relative to the mass of the drift gas molecule. The resulting chromatogram is compared to a library of known patterns to identify the substance collected. Since the collision cross section depends on more than one ion characteristic, peak identification is not unique. IMS systems measure a secondary and less specific property of the target molecule—the time it takes for the ionized molecule to drift through a tube filled with a viscous gas under an electric field—and the identity of the molecule is inferred from the intensity vs time spectrum.

Other mobility-based separation techniques include high-field asymmetric waveform ion mobility spectrometry (FAIMS) also known as Differential Mobility Spectrometry (DMS). FAIMS or DMS is a detection technology which can operate at atmospheric pressure to separate and detect ions. Compared to conventional ion mobility, FAIMS/DMS devices operate at much higher fields (~10,000 V/cm) where ion mobilities become dependent on the applied field. FAIMS/DMS devices may operate in conjunction with IMS drift tube devices in spectrometers having multiple stages. For specific descriptions of features and uses of instruments for ion detection and chemical analysis, including features of IMS drift tube devices used in connection with one or more FAIMS/DMS devices, among other components, reference is made to U.S. Pat. No. 8,173,959 B1 to Boumsellek et al., entitled "Real-Time Trace Detection by High Field and Low Field Ion Mobility and Mass Spectrometry," U.S. Pub. No. 2012/0273669 A1 to Ivashin et al., entitled "Chemical Analysis Using Hyphenated Low and High Field Ion Mobility," and U.S. Pub. No. 2012/0326020 A1 to Ivashin et al., entitled "Ion Mobility Spectrometer Device with Embedded FAIMS," which are all incorporated herein by reference.

Known atmospheric pressure ionization devices, such as the ones used in IMS and DMS devices, may use a radioactive ionization source to generate the ions that are used in connection with the chemical analysis and detection processes. Still other known devices may use non-radioactive ionization techniques that include corona discharges and/or ultraviolet (UV) light and laser-induced ionization. In connection with the above-noted techniques, reference is made, for example, to U.S. Pat. No. 8,440,981 to Bromberg et al., entitled "Compact Pyroelectric Sealed Electron Beam," U.S. Pat. No. 6,429,426 to Döring, entitled "Ionization Chamber with Electron Source," and U.S. Pat. No. 5,969,349 to Budovich et al., entitled "Ion Mobility Spectrometer," all of which are incorporated herein by reference.

Fieldable trace detection of illicit substances, particularly explosives and narcotics, is challenging primarily due to the wide range of volatility and to the electro-chemical properties of these compounds. While common explosives consist of nitro compounds detectable in negative mode since they form stable negative ions under condition of ambient pressure, some emerging higher volatility improvised explosives devices (IEDs) and homemade explosives (HMEs) are known to have high proton affinities in the form of adduct ions sometimes in the presence of chemical modifiers.

Accordingly, it would be desirable to provide for ion analysis techniques using an ionization source that provides the flexibility required to optimize the detection performance for a broad range of substances with different physical and chemical properties.

SUMMARY OF THE INVENTION

According to the system described herein, an ion analysis device includes an ion source, the ion source including a spark ion source. A controller controls a switching frequency of voltage changes of electrodes of the ion source in order to push positive and negative ions generated by spark discharge from the ion source. An ion mobility device may be provided into which the ions are injected from the ion source. The ion mobility device may includes an ion mobility spectrometry (IMS) device, a drift cell and/or a differential mobility spectrometry (DMS) device. A vacuum interface may be provided via which the ions are injected from the ion source into an analysis component. The controller may include a high voltage switching circuit. The ion source may have a point-to-point electrode configuration or a point-to-plane electrode configuration. The controller may control the switching frequency of the ion source according to real time or non-real time analysis and/or the controller may control the switching frequency the ion source according to an intended duty cycle. The switching frequency may be controlled to provide a pulsed or a continuous stream of ions from the ion source.

According further to the system described herein, a method of controlling ionization processing includes determining a mode of operation for ion analysis. A switching frequency of voltage changes of electrodes of an ion source may be determined, the ion source including a spark ion source. The voltage changes of electrodes of the ion source may be controlled during spark ionization according to the determined switching frequency using a controller in order to push positive and negative ions generated by spark discharge from the ion source. The method may further include injecting the ions generated by the ion source into an ion mobility device. The ion mobility device may include an ion mobility spectrometry (IMS) device, a drift cell and/or a differential mobility spectrometry (DMS) device. The method may further include injecting the ions generated by the ion source via a vacuum interface into an analysis component. The controller may include a high voltage switching circuit. The ion source may have a point-to-point electrode configuration or a point-to-plane electrode configuration. The controller may control the switching frequency of the ion source according to real time or non-real time analysis and/or the controller may control the switching frequency of the ion source according to an intended duty cycle. The switching frequency may be controlled to provide a pulsed or a continuous stream of ions from the ion source.

According further to the system described herein, a non-transitory computer-readable medium stores software for controlling ionization processing. The software may include executable code that determines a mode of operation for ion mobility spectrometry. Executable code is provided that determines a switching frequency of voltage changes of electrodes of an ion source, the ion source including a spark ion source. Executable code is provided that controls the switching frequency of the ion source using a controller in order to push positive and negative ions generated by spark discharge from the ion source. Executable code may be provided that controls injection of the ions generated by the ion source into an ion mobility device. Executable code may be provided that controls selective filtering of the ions after injection into the ion mobility device. Executable code may be provided that controls injection of the ions generated by the spark ionization into an analysis component via a vacuum interface. Executable code may be provided that controls analysis of the ions received from the vacuum interface at the analysis component. The switching frequency may be controlled using a high voltage switching circuit. The switching frequency of the ion source may be controlled according to real time or non-real time analysis and/or according to an intended duty cycle. The switching frequency may be controlled to provide a pulsed or a continuous stream of ions from the ion source.

BRIEF DESCRIPTION OF THE DRAWINGS

Embodiments of the system described herein are explained with reference to the several figures of the drawings, which are briefly described as follows.

DETAILED DESCRIPTION OF VARIOUS EMBODIMENTS

According to the system described herein, devices and techniques for ion analysis, including ion mobility separation and mass spectrometry, are provided using a dual polarity spark ion source are provided using a dual polarity spark ion source and having the flexibility required to optimize the detection performance for a broad range of illicit substances with different physical and chemical properties. In various embodiments, the volatility and electro-chemical aspects may be addressed by the system described herein by performing real-time detection of compounds detectable in both positive and negative polarities and/or prioritizing spectra acquisition in a given polarity due to the high volatility and therefore short residence of certain target compounds.

Figure 1:
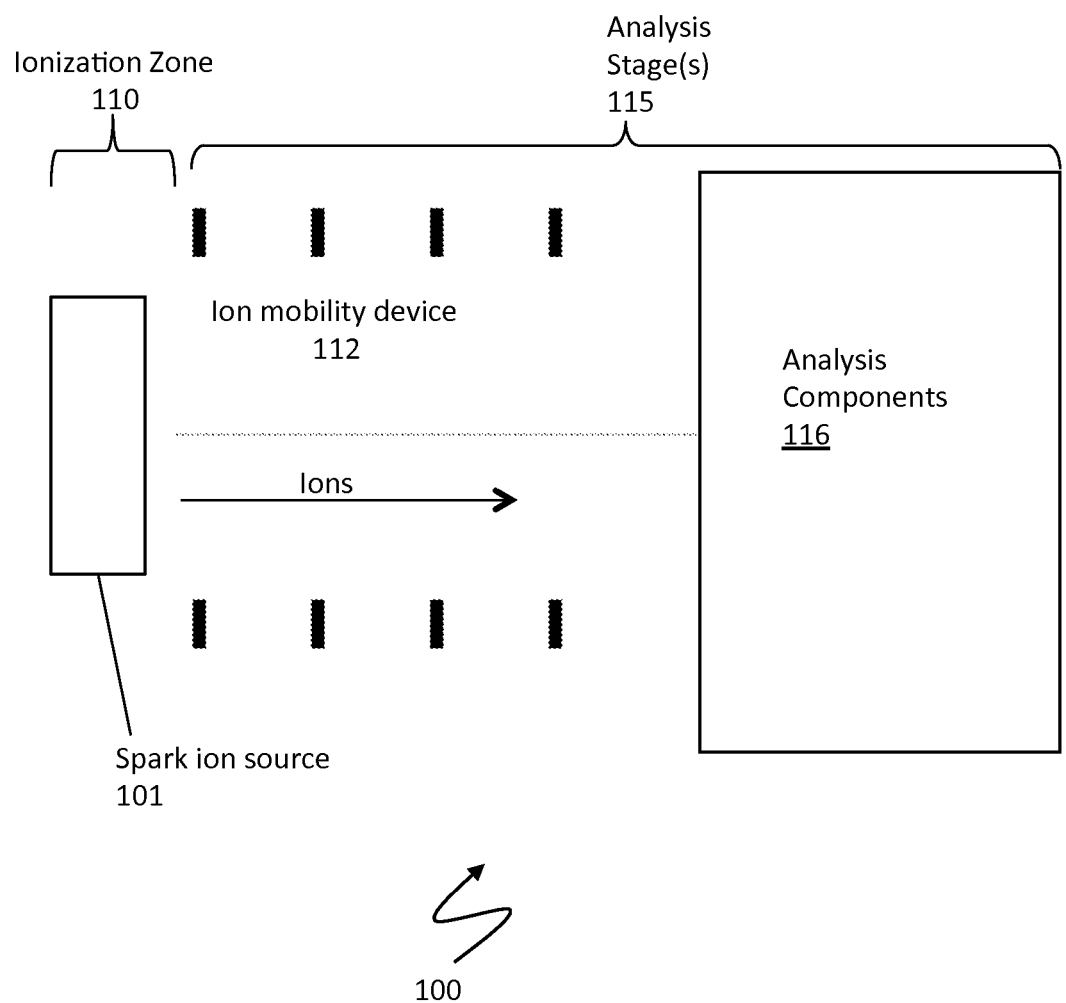
FIG. 1 is a schematic illustration showing a real-time dual polarity ion analysis device having a variable frequency spark ion source and an ion mobility device and analysis components according to an embodiment of the system described herein.

FIG. 1 is a schematic illustration showing a real-time dual polarity ion analysis device 100 having a variable frequency, non-radioactive, spark ion source 101, an ion mobility device 112, such as a single drift region or cell, and analysis components 116 according to an embodiment of the system described herein. Positive and negative ions, simultaneously generated during a spark discharge of the spark ion source 101, may be sequentially injected into the ion mobility device 112 for separation on the basis of their mobility. The spark discharge may be generated at or near atmospheric pressure between multiple electrodes, e.g., two, by creating strongly non-uniform fields and using a high voltage fast switching circuit. Point-to-plane and point-to-point electrode gap configurations are among the various possible embodiments of the spark ion source 101, as further discussed elsewhere herein.

The device 100 is shown including an ionization zone 110 that may include the spark ion source 101 and/or one or more sample regions with a sample to be analyzed, as further discussed elsewhere herein. Ions from the ionization zone 110 are injected into one or more ion mobility devices 112, such as a drift cell and/or other IMS or DMS mobility device. In various embodiments, the ions may be from a sample to be analyzed and/or may be reactive ions that are separate from a sample being analyzed and which will be used to react with sample molecules for analysis. Ion analysis may be performed in an analysis stage 115 having any one or more of a variety of analysis components 116 and including filtering components, as further discussed elsewhere herein. In various embodiments, the ion mobility components 112 and analysis components 116 of the analysis stage 115 may include IMS devices and/or drift cells, IMS-DMS combinations, IMS with embedded DMS, MS devices via a vacuum interface, any one or combination of ion mobility devices followed by MS, and/or any other appropriate combination.

Figure 2:
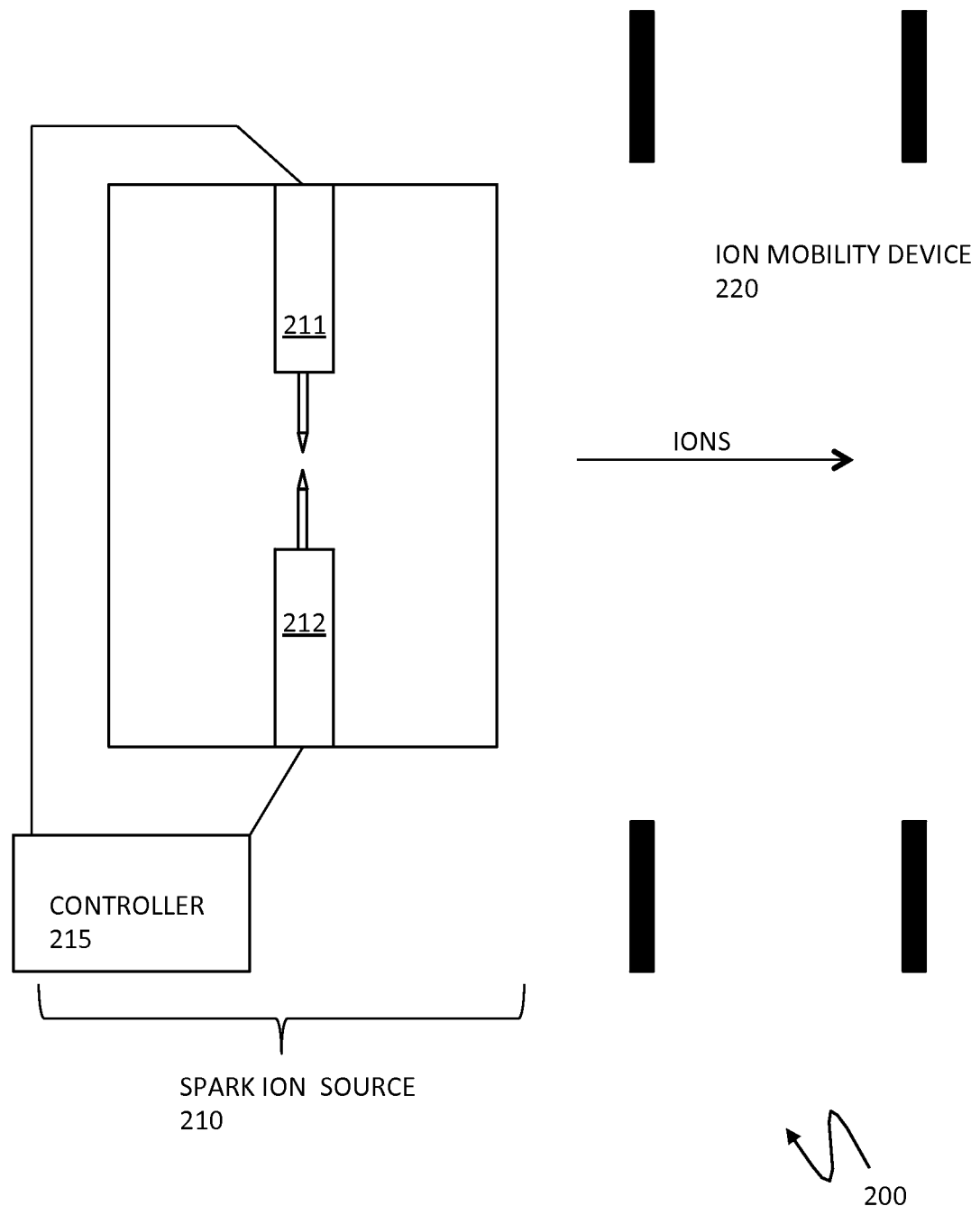
FIG. 2 is a schematic illustration showing an embodiment of a spark ion source and ion mobility device in an ion analysis device according to an embodiment of the system described herein.

FIG. 2 is a schematic illustration showing an embodiment of a spark ion source 210 and an ion mobility device 220 in an ion analysis device 200 according to an embodiment of the system described herein. The spark ion source 210 is shown schematically having electrodes 211, 212 in a point-to-point electrode configuration. Given the short time duration of the spark discharge (µs range), the polarity of the electrode(s) 211, 212 from which the spark is initiated may be controlled using a controller 215 to influence the breakdown processes, electric field strength, breakdown voltages, and ozone and nitrous oxide generation. The disclosed spark ion source 210 is able to operate over a wide range of frequencies. At low frequencies the source may inject packets of ions into the drift cell after the completion of each spectrum of a selected time range. At high frequencies the source 201 may inject a continuous stream of ions for guidance, separation from neutrals, or subsequent analysis in a hyphenated stage such as MS, DMS and/or other spectrometer platforms, as further described elsewhere herein. Although an ion mobility device 220 is shown, the system described herein may be used to inject ions from the spark ion source 210 into any appropriate device for ion analysis.

In an embodiment, the controller 215 may include a computer controlled high voltage (e.g., 2500 V) fast switching circuit that is able to produce stable voltages during the analysis and rapidly switch polarity at any time after the completion of a spectrum of a selected time range. The polarity switching may be accomplished at a variable frequency which may be selected depending on the duty cycle intended.

For example, in an embodiment for a mode of operation corresponding to a 50% duty cycle, alternating the extraction voltage (e.g., from approximately +2500 V to −2500 V) with respect to a collector of the ion analysis device pushes positive and negative ions into the ion mobility device 220, respectively, and both ion mobility spectra are collected in real time. In this mode of operation, the switching frequency of the voltages of the electrodes may be determined by the time range of the mobility spectrum and the speed of the high voltage switching circuit of the controller 215. For example, for 55 ms ion mobility spectra and 20 ms polarity switching time, the frequency is about 13.33 Hz.

In another embodiment, a non-real-time 50% duty cycle may be accomplished by acquiring several spectra in one polarity prior to switching to the other polarity to acquire the same number of spectra. This mode minimizes the detector noise caused by the perturbations associated with excessive switching due to the capacitive coupling.

Other duty cycle modes of operation, including non-50% duty cycle operations, may include operating in either positive or negative mode for a period of time long enough, within the sampling cycle, to acquire several spectra in one polarity prior to switching polarity to acquire spectra in the other polarity. The timing of such mode may be optimized for recording spectra for evanescent volatile compounds early during the sampling cycle.

Figure 3:
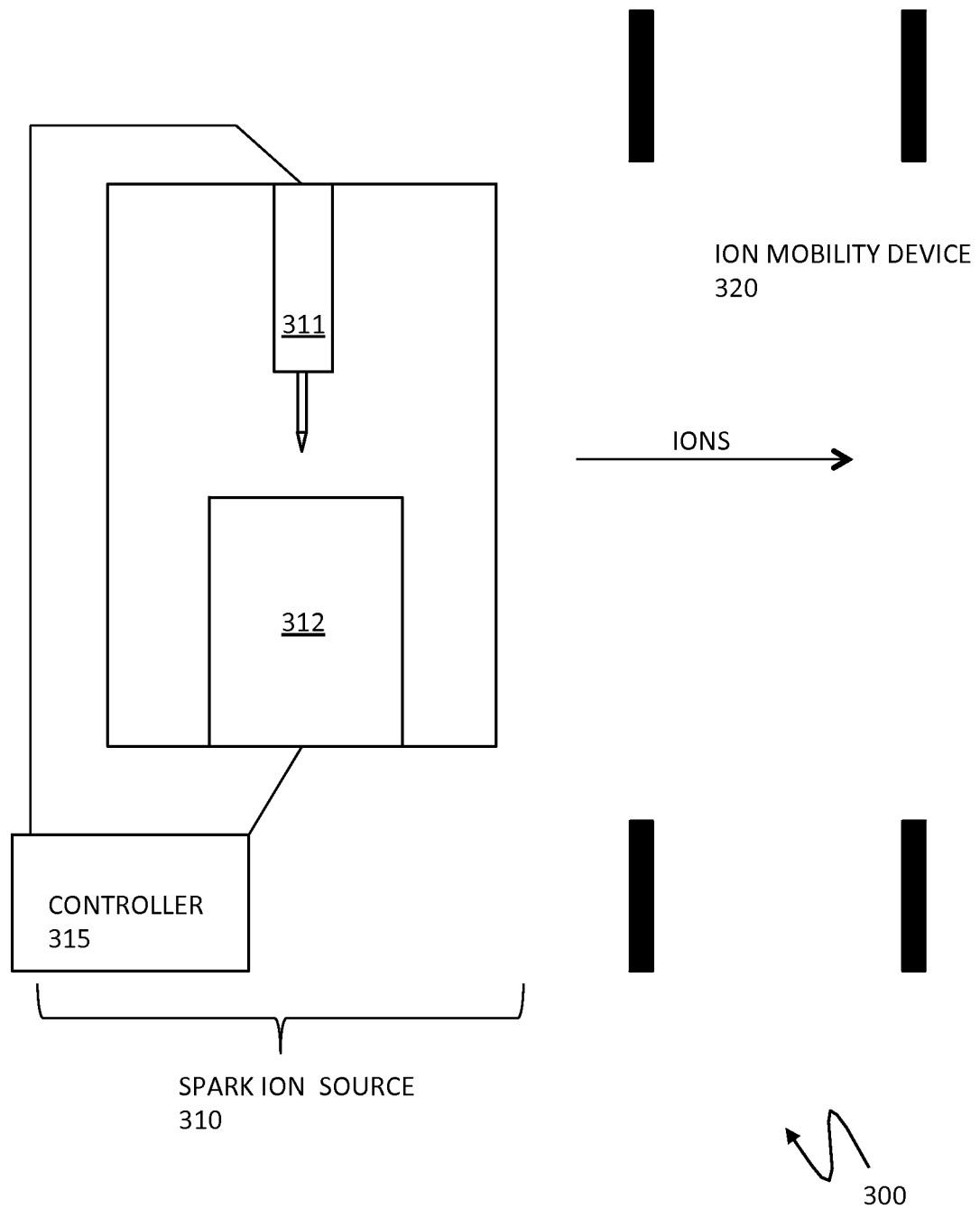
FIG. 3 is a schematic illustration showing an embodiment of a spark ion source and ion mobility device in an ion analysis device according to another embodiment of the system described herein.

FIG. 3 is a schematic illustration showing an embodiment of a spark ion source 310 and an ion mobility device 320 in an ion analysis device 300 according to another embodiment of the system described herein. The spark ion source 310 is shown schematically having electrodes 311, 312 in a point-to-plane electrode configuration. Other electrode configurations of the spark ion source 310 may be used in connection with the system described herein. Although an ion mobility device 320 is shown, the system described herein may be used to inject ions from the spark ion source 310 into any appropriate device for ion analysis.

In various embodiments, the system described herein may be used in connection with tandem instruments, namely using a spark ionization source and two separation techniques, such as low and high field mobility techniques. It is noted that, in various embodiments, the tandem instruments may be orthogonal to each other, specifically in which the flow directions of ions in the low field (IMS) and high field (DMS) mobility devices are orthogonal, and/or the DMS device may be embedded in the IMS drift cell and in which the flow directions of ions may be co-axial along the IMS and DMS devices. The DMS cell may include two parallel grids (e.g., planar and/or non-planar grids) of approximately the same diameter as the IMS rings and can be placed anywhere along a drift tube and biased according to their location in the voltage divider ladder to create the same IMS field. The spacing between the grids constitutes the analytical gap where ions are subject, in addition to the drift field, to the asymmetric dispersive field of the DMS. The oscillatory motion performed during the high and low voltages of the asymmetric waveform separates the ions according to the difference in their mobilities.

Figure 4:
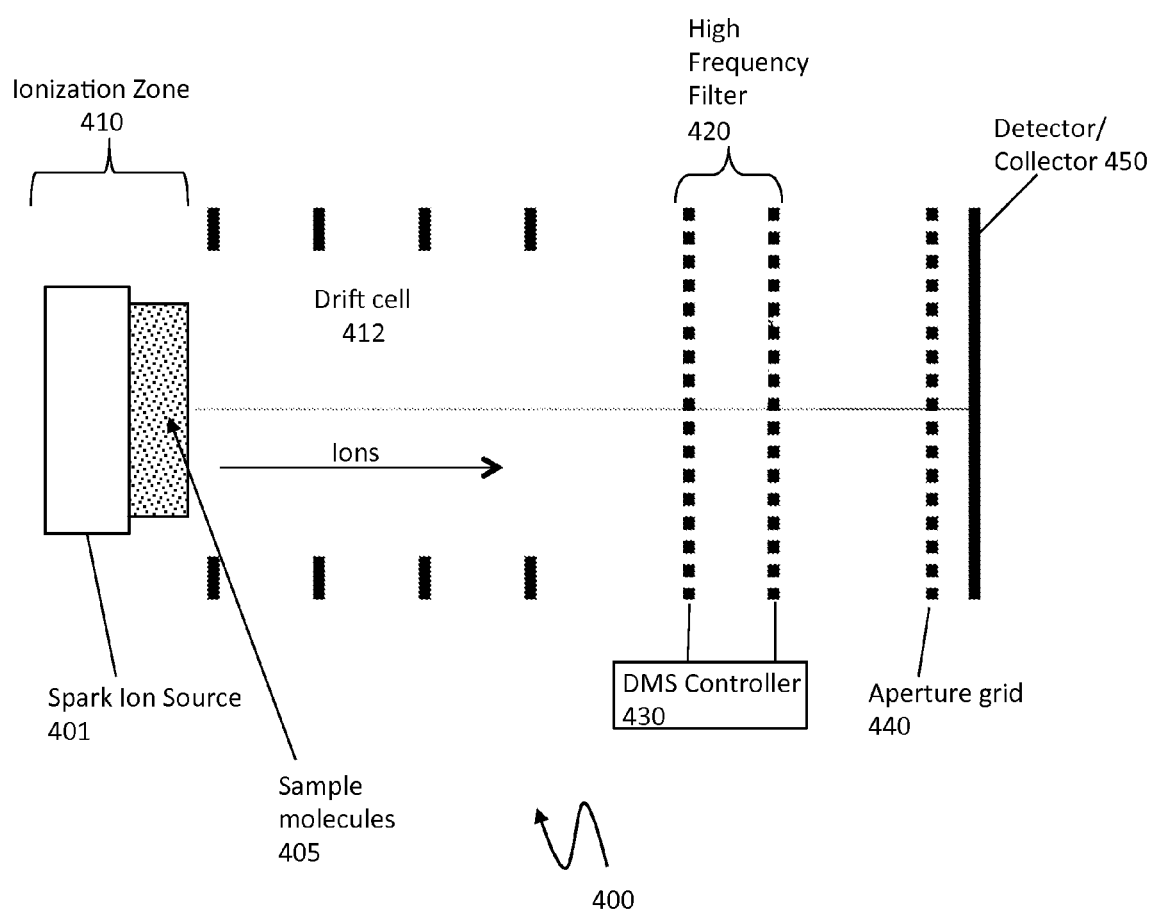
FIG. 4 is a schematic illustration showing an embodiment for an ion analysis device including ion filtering according to the system described herein.

FIG. 4 is a schematic illustration showing an embodiment for an ion analysis device 400 including ion filtering according to the system described herein. The ion analysis device 400 may include a spark ion source 401 in an ionization zone 410. In an embodiment, the ionization zone 410 may include a sample zone of sample molecules 405 that interact with the ions of the spark ion source 401 to generate ions of interest that are injected into an analysis stage, having one or more ion mobility devices, such as a drift cell 412, for analysis. In connection with the illustrated embodiment, components of an analysis stage of the device 400 may include a high frequency filter 420 positioned after the ionization zone 410. After passing through the high frequency filter 420, ions of interest may then travel through an aperture grid 440 to a detector/collector assembly 450 for analysis according to an embodiment of the system described herein.

The high frequency filter 420 may be used in connection with the spark discharge ionization in the ionization zone 410, as further discussed elsewhere herein. The high frequency filter 420 may include a cell made of two parallel grids of various shapes, including cylindrical, spherical, and planar. In an embodiment, the filter may be a FAIMS cell. Within the cell, in the analytical gap between the parallel grids, the combination of drift and high frequency asymmetric axial fields is applied. The high frequency field alternates between high and low fields and subjecting ions to oscillations within the cell. Ions are either accelerated or decelerated depending on the nature of their high field mobility. Applying a small DC voltage can filter out specific ions on the basis of differences between their low and high field mobilities. In the illustrated embodiment, the high frequency filter 420 is shown after the ionization zone 410. By applying specific DC voltages, controlled by a DMS controller 430, the high frequency filter 420 may be used to control ion mobility. It is noted that, in various embodiments, the DMS controller 430 may be coupled to and/or integrated with the spark ion source controller 215, 315 discussed elsewhere herein. This method can be used to generate the ions of choice for subsequent analysis in such platforms as ion mobility and differential mobility spectrometers. In various embodiments, sample molecules of interest are ionized in the ionization zone 410 for direct filtering, collection and analysis, whereas in other embodiments, reactive ions may be generated and a later charge transfer process is used to generate ions of interest for analysis in a sample zone.

In other embodiments, it is noted that the high frequency filter 420 may be mounted before or after the drift cell 412 and/or other ion mobility device that provides for ion separation after injection from the ionization source 401, as further discussed elsewhere herein. In other embodiments, the high frequency filter 420 may be mounted anywhere along a length of the drift cell 412. It is specifically noted that other ion analysis techniques and configurations may be used in connection with the system described herein.

For more detailed descriptions of features and uses of instruments that include one or more FAIMS/DMS devices and that may be used in connection with ion detection and chemical analysis techniques, reference is made to U.S. Patent App. Pub. No. 2012/0273669 A1 to Ivashin et al., entitled "Chemical Analysis Using Hyphenated Low and High Field Ion Mobility" and U.S. Patent App. Pub. No. 2012/0326020 A1 to Ivashin et al., entitled "Ion Mobility Spectrometer Device with Embedded FAIMS," which are both incorporated herein by reference. Reference is also made to U.S. Pat. No. 8,173,959 to S. Boumsellek et al., entitled "Real-Time Trace Detection by High Field and Low Field Ion Mobility and Mass Spectrometry," which is incorporated herein by reference.

Figure 5:
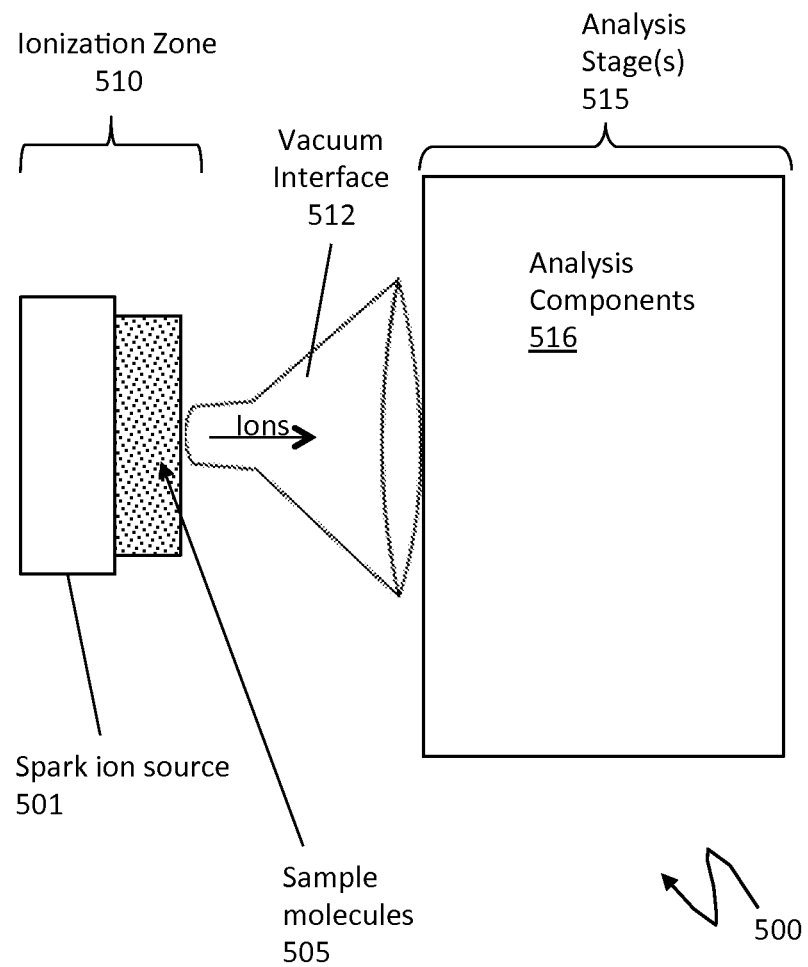
FIG. 5 is a schematic illustration showing an embodiment for an ion analysis device including a vacuum interface according to the system described herein.

FIG. 5 is a schematic illustration showing an embodiment for an ion analysis device 500 including a vacuum interface 512 according to the system described herein. Ions generated in an ionization zone 510, including a spark ion device 501 and/or a sample zone for sample molecules 505, like that discussed elsewhere herein, may be injected via the vacuum interface 512 into one or more analysis components 516 of an analysis stage 515. In various embodiments, the analysis components 516 may include an MS device, an ion mobility device and/or a combination of one or more ion mobility devices and an MS device.

Figure 6:
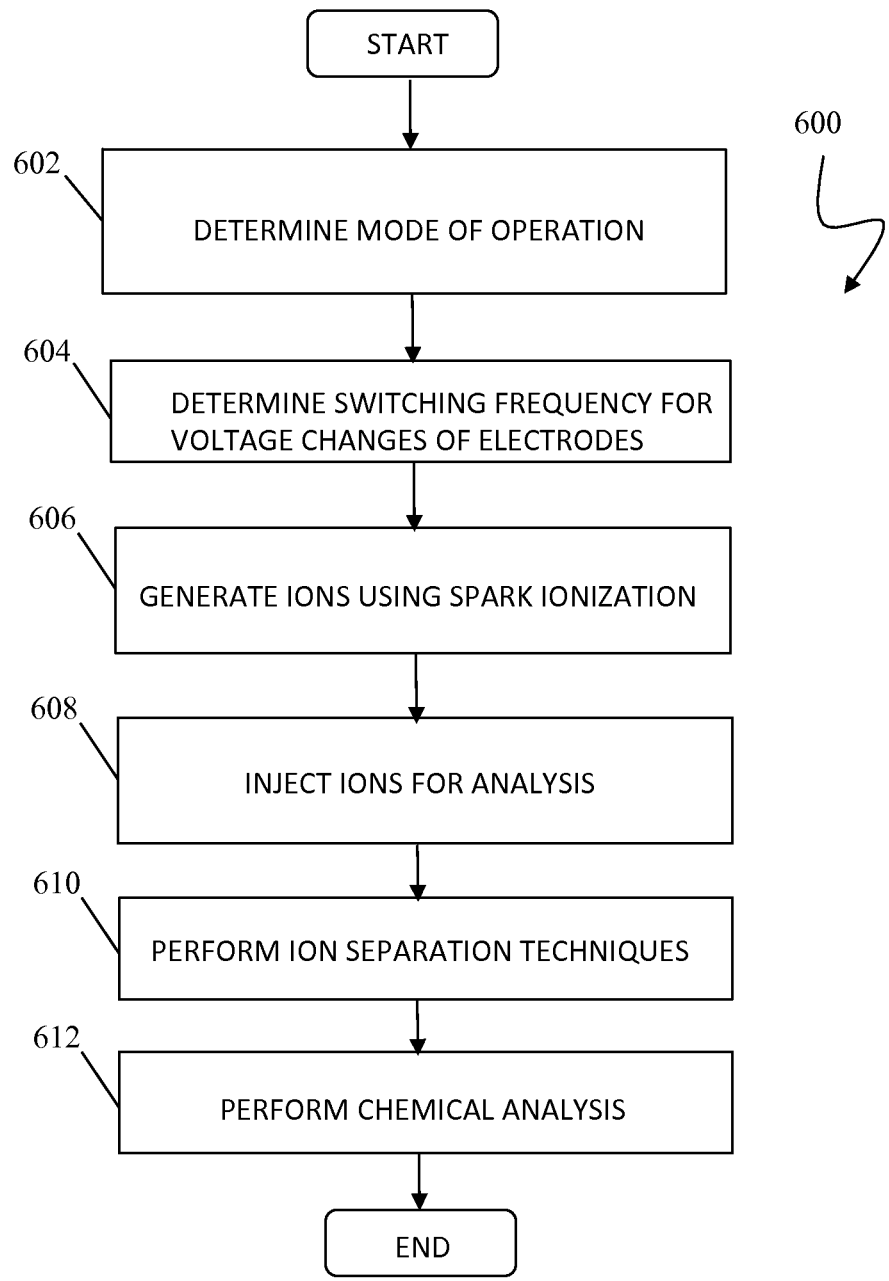
FIG. 6 is a flow diagram showing ion mobility spectrometry analysis processing using dual polarity spark ionization according to an embodiment of the system described herein.

FIG. 6 is a flow diagram 600 showing ion mobility spectrometry analysis processing using dual polarity spark ionization according to an embodiment of the system described herein. At a step 602, a mode of operation is determined for an ion mobility spectrometry device using spark ionization according to the system described herein. Determining the mode of operation may include determining real time or non-real time operation and the duty cycle (e.g., 50% or non-50% duty cycle). The mode may be determined based on optimization factors for recording spectra for evanescent volatile compounds during the sampling cycle. After the step 602, at a step 604, a switching frequency of the electrode voltages of the spark ion source may be determined and may be selected depending on the duty cycle intended and in order to push positive and negative ions generated by spark discharge from the ion source. At low frequencies the source may inject packets of ions into the drift cell after the completion of each spectrum of a selected time range. At high frequencies the source may inject a continuous stream of ions for guidance, separation from neutrals, or subsequent analysis in hyphenated platforms. In an embodiment, a computer controlled high voltage fast switching circuit is provided that is able to produce stable voltages during the analysis and rapidly switch polarity at any time after the completion of a spectrum of the selected time range. For example, for 55 ms ion mobility spectra and 20 ms polarity switching time, the frequency of voltage switching of the electrodes is about 13.33 Hz.

After the step 604, at a step 606 ions are generated by spark ionization using the controlled dual polarity spark ionization source, controlled according to the switching frequency. The ions may be reactive ions that then interface with sample molecules to generate ions of interest for analysis. After the step 606, at a step 608 the ions are injected into an analysis stage. In various embodiments, the analysis stage may include a drift cell of an ion mobility spectrometer, injected into other types of ion mobility devices and/or the ions may be injected into a vacuum interface for analysis in an MS device. After the step 608, at a step 610 ion separation techniques may be performed on the ions, including the use of filtering techniques and tandem devices hyphenated stages such as MS, DMS and/or other spectrometer platforms, as further described elsewhere herein. After the step 610, at a step 612 chemical analysis is performed to detect a desired substance of a range of substances with different physical and chemical properties. After the step 612, processing is complete for the described iteration of processing.

Various embodiments discussed herein may be combined with each other in appropriate combinations in connection with the system described herein. Additionally, in some instances, the order of steps in the flow diagrams, flowcharts and/or described flow processing may be modified, where appropriate. Further, various aspects of the system described herein may be implemented using software, hardware, a combination of software and hardware and/or other computer-implemented modules or devices having the described features and performing the described functions. The system may further include a display and/or other computer components for providing a suitable interface with a user and/or with other computers.

Software implementations of aspects of the system described herein may include executable code that is stored in a computer-readable medium and executed by one or more processors. The computer-readable medium may include volatile memory and/or non-volatile memory, and may include, for example, a computer hard drive, ROM, RAM, flash memory, portable computer storage media such as a CD-ROM, a DVD-ROM, an SD card, a flash drive or other drive with, for example, a universal serial bus (USB) interface, and/or any other appropriate tangible or non-transitory computer-readable medium or computer memory on which executable code may be stored and executed by a processor. The system described herein may be used in connection with any appropriate operating system.

Other embodiments of the invention will be apparent to those skilled in the art from a consideration of the specification or practice of the invention disclosed herein. It is intended that the specification and examples be considered as exemplary only, with the true scope and spirit of the invention being indicated by the following claims.

What is claimed is:

1. An ion analysis device, comprising:
an ion source, the ion source including a spark ion source with a plurality of electrodes, at least a first electrode and a second electrode in the plurality being separated by a gap and configured to permit a spark discharge therebetween; and
a controller that controls a switching frequency of voltage changes to the electrodes of the ion source in order to alternatively push positive ions and negative ions generated by spark discharge from the ion source, wherein the controller includes a computer controlled high voltage fast switching circuit that is able to produce stable voltages during analysis and rapidly switch polarity of the first electrode and the second electrode at any time after completion of a spectrum and wherein the positive ions are pushed in response to the controller providing a first polarity to the first electrode and the second electrode and the negative ions are pushed in response to the controller providing a second polarity to the first electrode and the second electrode that is opposite of the first polarity.

2. The device according to claim 1, further comprising:
an ion mobility device into which the ions are injected from the ion source.

3. The device according to claim 2, wherein the ion mobility device includes at least one of: an ion mobility spectrometry (IMS) device, a drift cell or a differential mobility spectrometry (DMS) device.

4. The device according to claim 1, further comprising:
a vacuum interface into which the ions are received from the ion source; and an analysis component that receives the ions from the vacuum interface.

5. The device according to claim 1, wherein polarity switching is provided at a variable frequency which may be selected depending on a duty cycle intended.

6. The device according to claim 1, wherein the ion source has a point-to-point electrode configuration or a point-to-plane electrode configuration.

7. The device according to claim 1, wherein the controller controls the switching frequency of the ion source according to real time or non-real time analysis.

8. The device according to claim 1, wherein the controller controls the switching frequency of the ion source according to an intended duty cycle.

9. The device according to claim 1, wherein the controller controls the switching frequency to provide a pulsed or a continuous stream of ions from the ion source.

10. A method of controlling ionization processing, comprising:
determining a mode of operation for ion analysis;
determining a switching frequency of voltage changes of electrodes of an ion source, the ion source including a spark ion source with a plurality of electrodes, at least a first electrode and a second electrode in the plurality being separated by a gap and configured to permit a spark discharge therebetween; and
controlling the voltage changes of the electrodes of the ion source during spark ionization according to the determined switching frequency using a controller in order to alternatively push positive ions and negative ions generated by spark discharge from the ion source, wherein the controller includes a computer controlled high voltage fast switching circuit that is able to produce stable voltages during analysis and rapidly switch polarity of the first electrode and the second electrode at any time after completion of a spectrum and wherein the positive ions are pushed in response to the controller providing a first polarity to the first electrode and the second electrode and the negative ions are pushed in response to the controller providing a second polarity to the first electrode and the second electrode that is opposite of the first polarity.

11. The method according to claim 10, further comprising:
injecting the ions generated by the ion source into an ion mobility device.

12. The method according to claim 11, wherein the ion mobility device includes at least one of: an ion mobility spectrometry (IMS) device, a drift cell or a differential mobility spectrometry (DMS) device.

13. The method according to claim 10, further comprising:
using a vacuum interface to inject the ions generated by the ion source into an analysis component.

14. The method according to claim 10, wherein polarity switching is provided at a variable frequency which may be selected depending on a duty cycle intended.

15. The method according to claim 10, wherein the ion source has a point-to-point electrode configuration or a point-to-plane electrode configuration.

16. The method according to claim 10, wherein the controller controls the switching frequency of the ion source according to real time or non-real time analysis.

17. The method according to claim 10, wherein the controller controls the switching frequency of the ion source according to an intended duty cycle.

18. The method according to claim 10, wherein the switching frequency is controlled to provide a pulsed or a continuous stream of ions from the ion source.

19. A non-transitory computer-readable medium storing software for controlling ionization processing, the software comprising:
executable code that determines a mode of operation for ion analysis;
executable code that determines a switching frequency of voltage changes of electrodes of an ion source, the ion source including a spark ion source with a plurality of electrodes, at least a first electrode and a second electrode in the plurality being separated by a gap and configured to permit a spark discharge therebetween; and
executable code that controls the voltage changes to the electrodes of the ion source during spark ionization according to the determined switching frequency using a controller in order to alternatively push positive ions and negative ions generated by spark discharge from the ion source, wherein the controller includes a computer controlled high voltage fast switching circuit that is able to produce stable voltages during analysis and rapidly switch polarity of the first electrode and the second electrode at any time after completion of a spectrum and wherein the positive ions are pushed in response to the controller providing a first polarity to the first electrode and the second electrode and the negative ions are pushed in response to the controller providing a second polarity to the first electrode and the second electrode that is opposite of the first polarity.

20. The non-transitory computer-readable medium according to claim 19, wherein the software further comprises:
executable code that controls injection of the ions generated by the ion source into an ion mobility device.

21. The non-transitory computer-readable medium according to claim 20, wherein the software further comprises:
executable code that controls selective filtering of the ions after injection into the ion mobility device.

22. The non-transitory computer-readable medium according to claim 19, further comprising:
executable code that controls injection of the ions generated by the ion source into an analysis component via a vacuum interface.

23. The non-transitory computer-readable medium according to claim 19, wherein polarity switching is provided at a variable frequency which may be selected depending on a duty cycle intended.

24. The non-transitory computer-readable medium according to claim 19, wherein the switching frequency of the ion source is controlled according to real time or non-real time analysis.

25. The non-transitory computer-readable medium according to claim 19, wherein the switching frequency of the ion source is controlled according to an intended duty cycle.

26. The non-transitory computer-readable medium according to claim 19, wherein the switching frequency is controlled to provide a pulsed or a continuous stream of ions from the ion source.

27. The device according to claim 1, wherein the controller causes the electrodes to have a first polarity to acquire a plurality of spectra prior to automatically switching the electrodes to an opposite polarity to acquire spectra in the opposite polarity.

28. The method according to claim 10, further comprising:
the controller causing the electrodes to have a first polarity to acquire a plurality of spectra prior to automatically switching the electrodes to an opposite polarity to acquire spectra in the opposite polarity.

29. The non-transitory computer-readable medium according to claim 19, wherein the software further comprises:

executable code that causes the electrodes to have a first polarity to acquire a plurality of spectra prior to automatically switching the electrodes to an opposite polarity to acquire spectra in the opposite polarity.

* * * * *